(12) United States Patent
Farrow et al.

(10) Patent No.: US 8,216,576 B2
(45) Date of Patent: Jul. 10, 2012

(54) METHOD FOR INHIBITING BINDING TO B-CELL RECEPTOR

(75) Inventors: Stuart Neville Farrow, Stevenage (GB); Allard Kaptein, Stevenage (GB); Jeremy David Alistair Kitson, Stevenage (GB); Alison J. Winder, Stevenage (GB)

(73) Assignee: Glaxo Group Limited (GB)

( * ) Notice: Subject to any disclaimer, the term of this patent is extended or adjusted under 35 U.S.C. 154(b) by 501 days.

(21) Appl. No.: 11/745,684

(22) Filed: May 8, 2007

(65) Prior Publication Data
US 2009/0098129 A1    Apr. 16, 2009

Related U.S. Application Data

(63) Continuation of application No. 09/868,533, filed as application No. PCT/EP99/07303 on Oct. 5, 1999, now Pat. No. 7,399,593.

(30) Foreign Application Priority Data

Dec. 23, 1998  (GB) .................................. 9828628.9

(51) Int. Cl.
*A61K 39/00* (2006.01)
*A61K 39/395* (2006.01)
*C07K 16/18* (2006.01)
*C07K 16/24* (2006.01)

(52) U.S. Cl. ............... 424/139.1; 424/130.1; 424/141.1; 530/387.1; 530/387.9; 530/388.1; 530/388.23

(58) Field of Classification Search .................... None
See application file for complete search history.

(56) References Cited

U.S. PATENT DOCUMENTS

| | | | |
|---|---|---|---|
| 5,595,721 | A | 1/1997 | Kaminski et al. |
| 6,157,933 | A | 12/2000 | Shinopulos et al. |
| 6,403,770 | B1 | 6/2002 | Yu et al. |
| 6,881,401 | B1 * | 4/2005 | Yu et al. .................. 424/85.1 |

FOREIGN PATENT DOCUMENTS

| | | |
|---|---|---|
| EP | 0869180 | 10/1998 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/12964 | 3/1999 |
| WO | WO 00/43032 | 7/2000 |
| WO | WO 00/67034 | 11/2000 |
| WO | WO 01/12812 | 2/2001 |
| WO | WO 01/24811 | 4/2001 |
| WO | WO 02/066516 | 8/2002 |

OTHER PUBLICATIONS

Gruss, "Molecular, structural, and biological characteristics of the tumor necrosis factor ligand superfamily" Int'l Journal of Clinical and Laboratory Research, DE, Springer, Berlin 26(3):14-159 (1996) XP002094504.
U.S. Appl. No. 09/302,863, filed Apr. 30, 1999, Goodwin, et al.
U.S. Appl. No. 09/589,288, filed Jun. 8, 2000, Yu, et al.
U.S. Appl. No. 12/605,202, filed Oct. 23, 2009, Ruben, et al.
Bodmer, et al. trends in Biochem. Sci., vol. 27, No. 1, pp. 19-24, 2002.
Gras, et al., International Immunity, vol. 7, No. 7: 1093-1106, 1995.
Gross, et al., Nature 404:995-999 (Apr. 2000).
Gross, et al., Immunity 15:289,290 (Aug. 20001).
Hymowitz, et al., JBC vol. 280, No. 8, pp. 7218-7227, 2004.
Laabi, et al., EMBO Journal, vol. 11, No. 11: 3897-3904, 1992.
Laabi, et al., Nucleic Acids Research, vol. 22, No. 7: 1147-1154, 1994.
Mackay, et al., J. Exp. Med., vol. 190, No. 11, Dec. 6, 1999: pp. 1697-1710.
Madry, International Immunity, vol. 10, No. 11: 1693-1702, 1998.
Moore, et al., Science, vol. 285, Jul. 9, 1999: pp. 260-263.
Patel, et al., J. Biol. Chem., 2003, vol. 279: pp. 16727-16735.
Thompson, et al., J. Exp. Med. 192(1):129-135 (Jul. 2000).
Von Bulow, et al., Science 278: pp. 138-131, 1997.
Xia, et al., J. Exp. Med., 192(1):137-143 (Jul. 2000).

\* cited by examiner

*Primary Examiner* — Christine J Saoud
*Assistant Examiner* — Jon M Lockard
(74) *Attorney, Agent, or Firm* — Jonathan M. Dermott; William T. Han

(57) ABSTRACT

The invention provides an isolated protein which is a member of the TNF ligand superfamily and comprising: i) a polypeptide having the amino acid sequence of FIG. 1; or ii) a variant of the polypeptide of i).

5 Claims, 15 Drawing Sheets

FIG. 1

SEQ ID No. 1

RAVQGPEET

VTQDCLQLIADSETPTIQKGSYTFVPWLLS

FKRGSALEEKENKILVKETGYFFIYGQVLY

TDKTYAMGHLIQRKKVHVFGDELSLVTLFR
•
CIQNMPETLPNNSCYSAGIAKLEEGDELQL

AIPRENAQISLDGDVTFFGALKLL

FIG. 2
SEQ ID No. 2

MDDSTEREQSRLTSCLKKREE

MKLKECVSILPRKESPSVRSSKDGKLL<u>AAT</u>

<u>LLLALLSCCLTVVSFYQV</u>AALQGDLASLRA

ELQGHHAEKLPAGAGAPKAGLEETPAVTAG
•
LKIFEPPAPGEGNSSQNSRNKRAVQGPEET

VTQDCLQLIADSETPTIQKGSYTFVPWLLS

FKRGSALEEKENKILVKETGYFFIYGQVLY

TDKTYAMGHLIQRKKVHVFGDELSLVTLFR
•
CIQNMPETLPNNSCYSAGIAKLEEGDELQL

AIPRENAQISLDGDVTFFGALKLL

FIG. 3
SEQ ID No. 3
SEQ ID No. 9

```
                                          cgtgccgttcagggtccagaagaa
                                           R   A   V   Q   G   P   E   E
acagtcactcaagactgcttgcaactgattgcagac agtgaaacaccaactata caaaaa
 T   V   T   Q   D   C   L   Q   L   I   A   D  |S   E   T   P   T   I| Q   K
ggatcttacacatttgtt  ccatggcttctcagcttt  aaaaggggaagtgccctagaagaa
 G   S   Y   T   F   V  |P   W   L   L   S   F| K   R   G   S   A   L   E   E
aaagagaataaaatattg gtcaaagaaact ggttacttttttatatatggtcaggtttta
 K   E   N   K   I   L  |V   K   E   T| G   Y   F   F   I   Y   G   Q   V   L
tatactgataagacctacgccatgggacatctaattcagaggaagaaggtccatgtcttt
 Y   T   D   K   T   Y   A   M   G   H   L   I   Q   R   K   K   V   H   V   F
ggggatgaattgagtctggtgactttgtttcgatgtattcaaaatatgcctgaaacacta
 G   D   E   L   S   L   V   T   L   F   R   C   I   Q   N   M   P   E   T   L
cccaataattcctgctattcagctggcattgcaaaactggaagaaggagatggactccaa
 P   N   N   S   C   Y   S   A   G   I   A   K   L   E   E   G   D   G   L   Q
cttgcaataccaagagaa aatgcacaaatatcactggat ggagatgtcacattttttggt
 L   A   I   P   R   E  |N   A   Q   I   S   L   D| G   D   V   T   F   F   G
gcattgaaactgctgtga
 A   L   K   L   L   -
```

FIG. 4
SEQ ID No. 4
SEQ ID No. 10

```
atggatgactccacagaaagggagcagtcacgccttacttcttgccttaagaaaagagaa
 M  D  D  S  T  E  R  E  Q  S  R  L  T  S  C  L  K  K  R  E
gaaatgaaactgaaggagtgtgtttccatcctcccacggaaggaaagcccctctgtccga
 E  M  K  L  E  C  V  S  I  L  P  R  K  E  S  P  S  V  R
tcctccaaagacggaaagctgctggctgcaaccttgctgctggcactgctgtcttgctgc
 S  S  K  D  G  K  L  L  A  A  T  L  L  L  A  L  L  S  C  C
ctcacggtggtgtcttt ctaccaggtggccgccctgcaaggggacctggccagcctccgg
 L  T  V  V  S  F  Y  Q  V  A  A  L  Q  G  D  L  A  S  L  R
gcagagctgcagggccaccacgcggagaagctgccagcaggagcaggagcccccaaggcc
 A  E  L  Q  G  H  H  A  E  K  L  P  A  G  A  G  A  P  K  A
ggcctggaggaagctccagctgtcaccgcgggactgaaaatctttgaaccaccagctcca
 G  L  E  E  A  P  A  V  T  A  G  L  K  I  F  E  P  P  A  P
ggagaaggcaactccagtcagaacagcagaaataagcgtgccgttcagggtccagaagaa
 G  E  G  N  S  S  Q  N  S  R  N  K  R  A  V  Q  G  P  E  E
acagtcactcaagactgcttgcaactgattgcagadagtgaaacaccaactatacaaaaa
 T  V  T  Q  D  C  L  Q  L  I  A  D  S  E  T  P  T  I  Q  K
ggatcttacacatttgttccatggcttctcagctttaaaaggggaagtgccctagaagaa
 G  S  Y  T  F  V  P  W  L  L  S  F  K  R  G  S  A  L  E  E
aaagagaataaaatattggtcaaagaaactggttactttttatatatggtcaggtttta
 K  E  N  K  I  L  V  K  E  T  G  Y  F  F  I  Y  G  Q  V  L
tatactgataagacctacgccatggacatctaattcagaggaagaaggtccatgtcttt
 Y  T  D  K  T  Y  A  M  G  H  L  I  Q  R  K  K  V  H  V  F
ggggatgaattgagtctggtgactttgtttcgatgtattcaaaatatgcctgaaacacta
 G  D  E  L  S  L  V  T  L  F  R  C  I  Q  N  M  P  E  T  L
cccaataattcctgctattcagctggcattgcaaaactggaagaaggagatggactccaa
 P  N  N  S  C  Y  S  A  G  I  A  K  L  E  E  G  D  G  L  Q
cttgcaataccaagagaaaatgcacaaatatcactggatggagatgtcacattttttggt
 L  A  I  P  R  E  N  A  Q  I  S  L  D  G  D  V  T  F  F  G
gcattgaaactgctgtga
 A  L  K  L  L  -
```

FIG. 5
Seq ID No. 5

```
                                                IIQDCLQLI

ADSDTPTIRKGTYTFVPWLLSFKRGNALEEKENKIVVR

QTGYFFIYSQVLYTDPIFAMGHVIQRKKVHVFGDELSL
                       •
VTLFRCIQNMPKTLPNNSCYSAGIARLEEGDEIQLAIP

RENAQISRNGDDTFFGALKLL
```

FIG. 6
Seq ID No. 6

MDESAKTLPPPCLCFCSEKGED

MKVGYDPITPQKEEGAWFGICRDGR<u>LLAATLLLALLSS</u>

<u>SFTAMSLYQL</u>AALQADLMNLRMELQSYRGSATPAAAGA

PELTAGVKLLTPAAPRPHNSSRGHRNRRAFQGPEETEQ

DVDLSAPPAPCLPGCRHSQHDDNGMNLRNIIQDCLQLI

ADSDTPTIRKGTYTFVPWLLSFKRGNALEEKENKIVVR

QTGYFFIYSQVLYTDPIFAMGHVIQRKKVHVFGDELSL

VTLFRCIQNMPKTLPNNSCYSAGIARLEEGDEIQLAIP

RENAQISRNGDDTFFGALKLL

FIG. 7
Seq ID No. 7

```
                    atcattcaagactgtctgcagctgattgcagacagcgacacgccg
                     I  I  Q  D  C  L  Q  L  I  A  D  S  D  T  P
actatacgaaaaggaacttacacatttgttccatggcttctcagctttaaaagaggaaat
 T  I  R  K  G  T  Y  T  F  V  P  W  L  L  S  F  K  R  G  N
gccttggaggagaaagagaacaaaatagtggtgaggcaaacaggctatttcttcatctac
 A  L  E  E  K  E  N  K  I  V  V  R  Q  T  G  Y  F  F  I  Y
agccaggttctatacacggaccccatctttgctatgggtcatgtcatccagaggaagaaa
 S  Q  V  L  Y  T  D  P  I  F  A  M  G  H  V  I  Q  R  K  K
gtacacgtctttggggacgagctgagcctggtgaccctgttccgatgtattcagaatatg
 V  H  V  F  G  D  E  L  S  L  V  T  L  F  R  C  I  Q  N  M
cccaaaacactgcccaacaattcctgctactcggctggcatcgcgaggctggaagaagga
 P  K  T  L  P  N  N  S  C  Y  S  A  G  I  A  R  L  E  E  G
gatgagattcagcttgcaattcctcgggagaatgcacagatttcacgcaacggagacgac
 D  E  I  Q  L  A  I  P  R  E  N  A  Q  I  S  R  N  G  D  D
accttctttggtgccctaaaactgctgtaa
 T  F  F  G  A  L  K  L  L  -
```

FIG. 8
Seq ID No. 8

```
atggatgagtctgcaaagaccctgccaccaccgtgcctctgttttgctccgagaaagga
 M  D  E  S  A  K  T  L  P  P  P  C  L  C  F  C  S  E  K  G
gaagatatgaaagtgggatatgatcccatcactccgcagaaggaggagggtgcctggttt
 E  D  M  K  V  G  Y  D  P  I  T  P  Q  K  E  E  G  A  W  F
gggatctgcagggatggaaggctgctggctgctaccctcctgctggccctgttgtccagc
 G  I  C  R  D  G  R  L  L  A  A  T  L  L  L  A  L  L  S  S
agtttcacagcgatgtccttgtaccagttggctgccttgcaagcagacctgatgaacctg
 S  F  T  A  M  S  L  Y  Q  L  A  A  L  Q  A  D  L  M  N  L
cgcatggagctgcagagctaccgaggttcagcaacaccagccgccgcgggtgctccagag
 R  M  E  L  Q  S  Y  R  G  S  A  T  P  A  A  A  G  A  P  E
ttgaccgctggagtcaaactcctgacgccggcagctcctcgaccccacaactccagccgc
 L  T  A  G  V  K  L  L  T  P  A  A  P  R  P  H  N  S  S  R
ggccacaggaacagacgcgctttccagggaccagaggaaacagaacaagatgtagacctc
 G  H  R  N  R  R  A  F  Q  G  P  E  E  T  Q  D  V  D  L
tcagctcctcctgcaccatgcctgcctggatgccgccattctcaacatgatgataatgga
 S  A  P  P  A  P  C  L  P  G  C  R  H  S  Q  H  D  D  N  G
atgaacctcagaaacatcattcaagactgtctgcagctgattgcagacagcgacacgccg
 M  N  L  R  N  I  I  Q  D  C  L  Q  L  I  A  D  S  D  T  P
actatacgaaaaggaacttacacatttgttccatggcttctcagctttaaaagaggaaat
 T  I  R  K  G  T  Y  T  F  V  P  W  L  L  S  F  K  R  G  N
gccttggaggagaaagagaacaaaatagtggtgaggcaaacaggctatttcttcatctac
 A  L  E  E  K  E  N  K  I  V  V  R  Q  T  G  Y  F  F  I  Y
agccaggttctatacacggaccccatctttgctatgggtcatgtcatccagaggaagaaa
 S  Q  V  L  Y  T  D  P  I  F  A  M  G  H  V  I  Q  R  K  K
gtacacgtctttggggacgagctgagcctggtgaccctgttccgatgtattcagaatatg
 V  H  V  F  G  D  E  L  S  L  V  T  L  F  R  C  I  Q  N  M
cccaaaacactgcccaacaattcctgctactcggctggcatcgcgaggctggaagaagga
 P  K  T  L  P  N  N  S  C  Y  S  A  G  I  A  R  L  E  E  G
gatgagattcagcttgcaattcctcgggagaatgcacagatttcacgcaacggagacgac
 D  E  I  Q  L  A  I  P  R  E  N  A  Q  I  S  R  N  G  D  D
accttctttggtgccctaaaactgctgtaa
 T  F  F  G  A  L  K  L  L  -
```

FIG. 9

```
MOUSE   1 MDESAKTLPPPCLCFCSEKGEDMKVGYDPITPQKEEGAWFGICRDGRLLA  50
          ||:|  .      |  | .| |:||.         :.|         :||:|||
HUMAN   1 MDDSTER.EQSRLTSCLKKREEMKLKECVSILPRKESPSVRSSKDGKLLA  49

51 ATLLLALLSSSFTAMSLYQLAALQADLMNLRMELQSYRGSATPAAAGAPE 100
          ||||||||||   | .| ||.|||| || .|| |||  :      || |||| .
       50 ATLLLALLSCCLTVVSFYQVAALQGDLASLRAELQGHHAEKLPAGAGAPK  99

101 ........LTAGVKLLTPAAPRPHNSSRGHRNRRAFQGPEETEQDVDLSA 142
                  .|||.|:  | ||   |||.  ||:||  ||||||
      100 AGLEEAPAVTAGLKIFEPPAPGEGNSSQNSRNKRAVQGPEET........ 141

143 PPAPCLPGCRHSQHDDNGMNLRNIIQDCLQLIADSDTPTIRKGTYTFVPW 192
                                 :  ||||||||||:|||.||.||||||
      142 ......................VTQDCLQLIADSETPTIQKGSYTFVPW 168

193 LLSFKRGNALEEKENKIVVRQTGYFFIYSQVLYTDPIFAMGHVIQRKKVH 242
          |||||||.|||||||||.|::|||||||  ||||||   :||||.|||||||
      169 LLSFKRGSALEEKENKILVKETGYFFIYGQVLYTDKTYAMGHLIQRKKVH 218

243 VFGDELSLVTLFRCIQNMPKTLPNNSCYSAGIARLEEGDEIQLAIPRENA 292
          ||||||||||||||||||||.||||||||||||||:||||||:|||||||||
      219 VFGDELSLVTLFRCIQNMPETLPNNSCYSAGIAKLEEGDELQLAIPRENA 268

293 QISRNGDDTFFGALKLL* 310
          |||  .||  |||||||||||
      269 QISLDGDVTFFGALKLL* 286
```

METHOD FOR INHIBITING BINDING TO B-CELL RECEPTOR

CROSS-REFERENCE TO RELATED APPLICATIONS

This application is a continuation of U.S. patent application Ser. No. 09/868,533 filed Sep. 21, 2001 now U.S. Pat. No. 7,399,593, which is a 371 of International Application No. PCT/EP99/07303 filed on Oct. 5, 1999.

The present invention relates to a novel protein of the TNF ligand superfamily, nucleotides coding for it, vectors and host cells containing the same and methods of screening for modulators of the interaction between said protein and its receptor, said modulators for use in therapy for various disorders including, but not restricted to, cancer, inflammation, infection and autoimmune disease. Also, direct use of said ligand in therapy, for example against viral diseases or as a potential vaccine adjuvant.

Fifteen other members of the TNF ligand family have currently been cloned and published and most have been shown to bind to cell-surface receptors of the TNF receptor family. The interaction between a TNF ligand and its receptor is the key signal to start a chain of events leading to a range of responses as diverse as T-cell proliferation, apoptosis and induction of cytokine production. Some activities such as induction of T-cell proliferation are common to many members of the family, whilst some are shared by only a few, and others are unique. The interaction between these ligands and their receptors provides an attractive target for the development of novel therapies.

The present invention provides an isolated protein comprising i) a polypeptide having the amino acid sequence of FIG. 1 or ii) a variant of the polypeptide of i). The invention also provides an isolated protein comprising a polypeptide having the amino acid sequence as provided in FIG. 2 or variants thereof. The protein having the amino acid sequence provided in FIG. 2 is obtainable from humans and is a type II membrane protein with a single transmembrane domain near the N-terminus, which contains two potential N-linked glycosylation sites, and a protease cleavage site between amino acids arginine 133 and alanine 134. The polypeptide having the amino acid sequence provided in FIG. 1 is soluble, and forms part of the extracellular region of the polypeptide having the amino acid sequence provided in FIG. 2. Preferably the protein of the invention comprises a polypeptide which is 65%, preferably 75%, more preferably 80% and even more preferably 90% homologous to the amino acid sequence of FIG. 1. The protein of the invention most preferably comprises a polypeptide which is, at least 95%, for example 97%, 98% or 99% homologous to the amino acid sequence of FIG. 1. Preferably the protein of the invention is obtainable from mammals, more preferably from mice or humans, and most preferably from humans.

The present invention further provides a protein comprising a polypeptide which has the sequence as provided in FIG. 2 from amino acid 134 onwards, or the sequence as provided in FIG. 6 from amino acid 127 onwards.

The present invention further provides a protein comprising a polypeptide which has the sequence as provided in FIG. 2 from amino acid 122 onwards.

The present invention further provides a protein comprising a polypeptide which has the sequence as provided in FIG. 6 from amino acid 115 onwards.

The present invention further provides an isolated protein comprising a polypeptide having the amino acid sequence as provided in FIG. 5, or variants thereof. Moreover, the invention provides an isolated protein comprising a polypeptide having the amino acid sequence as provided in FIG. 6 or variants thereof. The protein having the amino acid sequence as provided in FIG. 6 is isolatable from mice and is a type II membrane protein with a single transmembrane domain near the N-terminus, which protein contains one potential N-linked glycosylation site, and a protease cleavage site between amino acids arginine 126 and alanine 127. The polypeptide having the amino acid sequence provided in FIG. 5 is soluble, and forms part of the extracellular region of the polypeptide having the amino acid sequence provided in FIG. 6.

Proteins of the invention isolatable from humans, and proteins of the invention isolatable from mice are highly homologous, displaying 67% amino acid identity over their entire sequence. In the C-terminal region involved in receptor binding, amino acid identity is much higher (87%). A significant difference between proteins of the invention isolatable from humans or mice is the presence of an additional exon in the mouse sequence encoding an extra 31 amino acids which reduces the overall homology between the two proteins.

The term variant refers to proteins which have substantially the same biological functionality as the protein for which sequence information has been provided. The term variant encompasses fragments, derivatives and analogues of the protein of the invention.

Fragments include portions of the protein which retain sufficient identity to the original protein to be effective for example in a screen.

Derivatives include alternate forms of the protein sequence which may have deletions, additions or substitutions of one or more amino acids. It will be understood by a person skilled in the art that certain substitutions, deletions or additions of amino acids can be made, or indeed can occur naturally, without substantially altering the function of the protein.

Analogues include but are not limited to precursor proteins which can be activated by cleavage of the precursor protein to produce an active mature protein, or a fusion with a leader or secretory sequence to aid purification.

The protein of the present invention may be a recombinant protein, a natural protein or a synthetic protein.

The proteins of the invention may be present in all embodiments in trimeric form and such trimers form an embodiment of the invention. Typically the proteins of the invention will bind to their receptor as a trimer, thus allowing two or more receptor molecules to be brought into proximity. A trimer may be a heterotrimer wherein more than one type of subunit is present, or a homotrimer wherein all subunits are the same.

The present invention also provides antibodies specific for the protein of the invention. The term antibody as used herein includes all immunoglobulins and fragments thereof which contain recognition sites for antigenic determinants of proteins of the present invention. The antibodies of the present invention may be polyclonal or monoclonal, may be intact antibody molecules or fragments containing the active binding region of the antibody, e.g. Fab or $F(ab)_2$. The present invention also includes chimeric, single chain and humanised antibodies and fusions with non-immunoglobulin molecules. Various procedures known in the art may be used for the production of such antibodies and fragments.

The proteins of the invention, their variants or cells expressing them can be used as an immunogen to produce antibodies thereto. Antibodies generated against the proteins of the invention can be obtained by direct injection of the polypeptide into an animal, preferably a non-human. The antibody so obtained will then bind the protein itself. In this manner, even a fragment of the protein of the invention can be used to generate antibodies binding the whole native protein.

The antibodies of the present invention may be used to locate the protein of the invention in tissue expressing that protein. They are also, for example, useful for purification of a protein of the invention, and accordingly there is provided a method of purifying a protein of the invention which method comprises the use of an antibody of the present invention. The antibodies of the present invention may also be used as therapeutic agents in their own right.

A further aspect of the invention provides an isolated polynucleotide which encodes a protein of the invention. Also included within the invention are anti-sense nucleotides or complementary strands. Preferably the nucleotide encodes a protein of the invention isolatable from a mouse or a human. More preferably the isolated polynucleotide comprises the polynucleotide portion having the nucleotide sequence shown in FIG. 3 (SEQ ID NO: 3), which codes for the polypeptide shown in FIG. 3 (SEQ ID NO: 9), a variant of said portion, or a complementary strand. The present invention further provides an isolated polynucleotide comprising the nucleotide sequence shown in FIG. 4 (SEQ ID NO: 4), which codes for the polypeptide of FIG. 4 (SEQ ID NO: 10).

The nucleotide sequence may be isolated from a cell (preferably a human cell), by screening with a probe derived from the protein of the invention, or by other methodologies known in the art such as polymerase chain reaction (PCR) for example on genomic DNA with appropriate oligonucleotide primers derived from or designed based on the protein of the invention. A bacterial artificial chromosome library can be generated using mouse or human DNA for the purposes of screening.

The nucleotide sequences of the present invention may be in the form of RNA or in the form of DNA, for example cDNA, genomic DNA, and synthetic DNA. Preferably the nucleotide sequence of the invention is cDNA. The DNA may be double-stranded or single-stranded, and if single stranded may be the coding strand or non-coding (anti-sense) strand. The coding sequence which encodes the protein of the invention may be identical to one of the coding sequences set forth in the Figures, or may be a different coding sequence which as a result of the redundancy or degeneracy of the genetic code, encodes the same protein as the sequences set forth therein.

A nucleotide sequence which encodes a protein of the present invention may include: a coding sequence for the protein or any variant thereof; a coding sequence for the protein or any variant thereof and additional coding sequence such as a leader or secretory sequence or a proprotein sequence; a coding sequence for the protein or any variant thereof (and optionally additional coding sequence) and non-coding sequences, such as introns or non-coding sequences 5' and/or 3' of the coding sequence for the full length protein.

The invention also provides nucleotide variants, analogues, derivatives and fragments which encode a protein of the invention. Nucleotides are included which preferably have at least 65% identity over their entire length to the nucleotide having the sequence of FIG. 3. More preferred are those sequences which have at least 75% identity over their entire length to the nucleotide having the sequence of FIG. 3. Even more preferred are polynucleotides which demonstrate at least 90%, for example 95%, 97%, 98% or 99% identity over their entire length to the nucleotide having the sequence of FIG. 3.

The nucleotide sequences of the invention may also have the coding sequence fused in frame to one or more marker sequences which allow for purification of the protein of the present invention such as a FLAG epitope, a myc sequence, or a secretory signal.

The nucleotide sequences of the present invention may be employed for producing a protein of the invention by recombinant techniques. Thus, for example the nucleotide sequence may be included in any one of a variety of expression vehicles or cloning vehicles, in particular vectors or plasmids for expressing a protein. Such vectors include chromosomal, non-chromosomal and synthetic DNA sequences. Examples of suitable vectors include derivatives of bacterial plasmids; phage DNA; yeast plasmids; vectors derived from combinations of plasmids and phage DNA and viral DNA. However, any other plasmid or vector may be used as long as it is replicable and viable in the host.

More particularly, the present invention also provides a vector comprising one or more of the nucleotide sequences as described above. The vectors are, for example, an expression vector, such as a plasmid or viral vector into which an isolated polynucleotide of the invention has been inserted, in a forward or reverse orientation. In a preferred aspect of this embodiment, the vector further comprises one or more regulatory sequences to direct mRNA synthesis, including, for example, a promoter, operably linked to the sequence. Suitable promoters include: CMV, LTR or SV40 promoter and other promoters known to control expression of genes in prokaryotic or eukaryotic cells or their viruses. The vector may contain an enhancer and a ribosome binding site for translation initiation and a transcription terminator.

Large numbers of suitable vectors and promoters/enhancers, will be known to those of skill in the art, but any plasmid or vector, promoter/enhancer may be used as long as it is replicable and functional in the host.

Appropriate cloning and expression vectors for use with prokaryotic and eukaryotic hosts include mammalian expression vectors, insect expression vectors, yeast expression vectors, bacterial expression vectors and viral expression vectors and are described in Sambrook et al., Molecular Cloning: A laboratory Manual, Second Edition, Cold Spring Harbor, N.Y., (1989) A preferred vector is pFLAG-CMV-1 or pcDNA3.

The vector may also include appropriate sequences for selection and/or amplification of expression. For this the vector will comprise one or more phenotypic selectable/amplifiable markers. Such markers are also well known to those skilled in the art.

In a further embodiment, the present invention provides host cells comprising a vector of the invention, and capable of expressing a nucleotide sequence of the invention. The host cells can be, for example, a higher eukaryotic cell, such as a mammalian cell or a lower eukaryotic cell, such as a yeast cell or a prokaryotic cell such as a bacterial cell. Suitable prokaryotic hosts for transformation include *E-coli*. Suitable eukaryotic hosts include HEK293T cells and HeLa cells.

Cell free translation systems can also be employed to produce such proteins using RNAs derived from the DNA constructs of the present invention.

Routine methods can be employed to purify the protein of the invention from recombinant cell cultures. Such methods are well understood by persons skilled in the art.

The proteins and nucleotide sequences of the present invention are provided in an isolated form. The term "isolated" is intended to convey that the material is not in its native state. Thus, the naturally-occurring nucleotide sequence or protein present in a living animal is in its native state and is not isolated, but the same nucleotide sequence or protein, separated from some or all of the materials it co-exists with in the natural system, is isolated. Similarly, a protein which has been produced by synthetic means, for example, by recombinant methods is "isolated." Such nucleotide sequence could be part of a vector. Such nucleotide sequence or protein could be part of a composition, and still be isolated in that such vector or composition is not part of its natural environment. The proteins and nucleotide sequences of the present invention are also preferably provided in purified form, and preferably are purified to at least 50% purity, more preferably about 75% purity, most preferably 90% purity or greater, such as 95%, 98% pure.

A further aspect of the present invention is the use of the proteins according to the invention in screening methods. Such methods identify compounds which act as modulators of the interaction between proteins of the invention and their receptor. In general terms, such screens will comprise contacting a protein of the invention, preferably in trimeric form, and its receptor in the presence or absence of the test compound, and measuring the increase or decrease in the level of binding, or increase or decrease in a response, for example NF-kB activation or CD40 activation, when the test compound is present. The proteins of the invention may be used in high throughput screens, thus enabling large numbers of compounds to be studied. The screening methods of the invention are generally well known to persons skilled in the art. The present invention also includes within its scope those compounds which are identified by the screening methods of the invention as possessing useful activity.

The present invention further provides compounds which are modulators of the interaction between a protein of the invention and its receptor for use in therapy, for example immunotherapy. The compounds are provided for use in the treatment of, for example, autoimmune disease, inflammation and other diseases associated with the activation of the transcription factor NF-κB, for example, rheumatoid arthritis, neuronal inflammation, asthma, in the treatment of cancers, in the treatment of infections, such as septic shock and in the treatment of atherosclerosis. The compounds may be agonists or antagonists of the receptor to which the proteins of the invention bind, but preferably are antagonists. The compounds include, for example, aptamers, polypeptides and small molecules.

The invention further provides the use of compounds which have been identified by the screening techniques of the invention, for the manufacture of a medicament for use in treatment or prophylaxis of disorders that are responsive to modulation of the interaction between the protein of the invention and its receptor.

The present invention additionally provides a method of treatment of a disorder which is responsive to modulation of the interaction between the protein of the invention and its receptor which comprises administering to a patient an effective amount of a compound identifiable by the screening techniques of the invention, or an effective amount of the protein of the invention.

The present invention further provides the protein of the invention for use in therapy, for example, for use in immunotherapy, particularly during viral infections, as a vaccine, or as a vaccine adjuvant.

The present invention also provides the use of the protein of the invention in the manufacture of a medicament for use in immunotherapy, for example, during viral infections, or as a vaccine adjuvant.

The present invention additionally provides a method of treatment of a disorder which is responsive to an increased amount of the protein of the invention which comprises administering to a patient an effective amount of the protein of the invention.

The invention also provides a nucleotide sequence as defined herein, for use in gene therapy or as a vaccine, for example, to increase the production of the protein of the invention in disorders which respond to an increased level of the protein of the sequence of FIG. 1 or FIG. 2. A patient may be provided with said nucleotide as a naked polynucleotide in the form of an expression vector such as a plasmid, or with a viral vector comprising said nucleotide, or a cell comprising said nucleotide or vector.

Complementary or anti-sense strands of the nucleotide sequences of the invention can also be used in gene therapy. For example, a cDNA sequence or fragments thereof could be used in gene therapy strategies to down regulate expression of the protein of the invention. Antisense technology can be used to control gene expression through triple-helix formation of antisense DNA or RNA, both of which methods are based on binding of a nucleotide sequence to DNA or RNA.

Suitable techniques for introducing the naked polynucleotide or vector into a patient include topical application with an appropriate vehicle. The naked polynucleotide or vector may be present together with a pharmaceutically acceptable excipient, such as phosphate buffered saline (PBS). One technique involves particle bombardment (which is also known as 'gene gun' technology and is described in U.S. Pat. No. 5,371, 015). Here inert particles (such as gold beads) are coated with a nucleic acid, and are accelerated at speeds sufficient to enable them to penetrate a surface of a recipient (e.g. skin), for example by means of discharge under high pressure from a projecting device. (Particles coated with a nucleic acid molecule of the present invention are within the scope of the present invention, as are devices loaded with such particles.) Other methods of administering the nucleic acid directly to a recipient include ultrasound, electrical stimulation, electroporation and microseeding which is described in U.S. Pat. No. 5,697,901.

Nucleic acid molecules of the present invention may also be administered by means of specialised delivery vectors useful in gene therapy. Gene therapy approaches are discussed for example by Verme et al, Nature 1997, 389:239-242. Both viral and non-viral systems can be used. Viral based systems include retroviral, lentiviral, adenoviral, adeno-associated viral, herpes viral and vaccinia-viral based systems. Non-viral based systems include direct administration of nucleic acids and liposome-based systems.

A nucleic acid sequence of the present invention may be administered by means of transformed cells. Such cells include cells harvested from a subject. The naked polynucleotide or vector of the present invention can be introduced into such cells in vitro and the transformed cells can later be returned to the subject. The polynucleotide of the invention may integrate into nucleic acid already present in a cell by homologous recombination events. A transformed cell may, if desired, be grown up in vitro and one or more of the resultant cells may be used in the present invention. Cells can be provided at an appropriate site in a patient by known surgical or microsurgical techniques (e.g. grafting, micro-injection, etc.)

The invention also relates to compositions comprising the polypeptide, polynucleotide, vector or transfected cell of the invention in addition to those which may be administered by gene gun. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Polypeptides, polynucleotides and other compounds of the present invention such as those identifiable by screening methods as described above may be employed alone or in conjunction with other compounds, such as therapeutic compounds. The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 µg/kg body weight. In most cases they will be administered in an amount not in excess of about 8 mg/kg body weight per day. Preferably, in most cases, dose is from about 10 µg/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The present invention further provides a method of producing a protein of the invention, which method comprises introducing into an appropriate cell line a vector comprising a polynucleotide as defined herein under conditions suitable for obtaining expression of the protein.

The present invention further provides a method of producing trimers comprising the protein of the invention, which method comprises introducing into an appropriate cell line a vector comprising a polynucleotide as defined herein under conditions suitable for obtaining expression of the protein, and allowing the protein produced to form into trimers.

As shown in Example 6, the protein of the invention binds to B cell lines such as the Burkitt Lymphoma cell line Raji, the B lymphoma cell line ROMI 8866 and PRMI8826. As shown in example 7, in preparations of whole blood, the protein of the invention binds only to B cells, not T cells. These examples confirm the presence of the receptor for the protein of the invention on B cells, and support the role of the protein of the invention in regulation of the immune system, and diseases as described above. This is also supported by the fact that the protein of the invention is strongly expressed in cells and tissues of the immune system as shown in example 5.

One of the first events induced by most members of the TNF ligand family is activation of NF-κB. Mukhopadhyay et al (Journal of Biological Chemistry Vol. 274 issue 23 Jun. 4, 1999, pp 15978-15981) have demonstrated that the protein of the invention can activate NF-κB in a dose and time dependent manner. The range of doses used was 1 pM to 1000 pM. Treatment of cells with as little as 1 pM of the protein of the invention produced an increase in NF-κB activation compared to untreated cells. The activation of this important transcription factor suggests that the protein of the invention may be involved in activation of inflammatory pathways, Molecules that modulate the interaction of the protein of the invention with its receptor will hence be able to modulate the activation of NF-κB and so will be useful in any diseases that are responsive to modulation of the level of activity of NF-κB, for example diseases of the immune system such as autoimmune disease, inflammatory diseases such as rheumatoid arthritis, neuronal inflammation and asthma and the proliferative diseases such as cancer. Mukhophadhyay et al further demonstrate that activation of NF-κB in the same system can be inhibited by antibodies specific to the protein of the invention. According to Mukhophadhyay et al, the protein of the invention was incubated with the specific antibodies before being used to treat cells. In contrast to the previous experiment, reduced activation of NF-κB was observed.

It is postulated that the presence of the antibody affects the binding of the protein of the invention to its receptor, thus preventing generation of a signal and consequently reducing NF-κB activation. These findings indicate that other compounds, for example small molecules, which modulate the interaction between the protein of the invention and its receptor can be identified in a screen and can be used to modulate NF-κB activation and other downstream effects.

In Example 9, Chromosomal localisation experiments show that the gene encoding the protein of the invention maps to human chromosome 13, region q33. No other TNF ligand family members have been mapped to this region. Abnormalities in this locus have been characterised in Burkitt Lymphomas as the second most frequent defect (Berger et al Genes Chromosomes Cancer. 1:115-118). Also, as shown in Example 6, the protein of the invention binds strongly to the Burkitt lymphoma cell line Raji, and Schneider et al (as referenced above) have demonstrated that the soluble form of the protein of the invention binds strongly to other Burkitt Lymphoma cell lines such as BJAB, Namalawa, Ramos and JIYOYE.

Mukhophadhy et al (as referenced above) have demonstrated that the protein of the invention is able to inhibit the growth of human tumour cell lines. Activation of NF-κB is an early cellular response which is generally followed by cytotoxic effects to tumour cells. By treating various cell lines with the protein of the invention and examining them for viability, the authors were able to show that there is a dose dependent decrease in the viability of cells in the presence of the protein of the invention. This was demonstrated for a human histiocytic lymphoma cell line, a prostate cancer cell line, a colon cancer cell line, a cervical carcinoma cell line and a breast carcinoma cell line.

These facts suggest that the protein of the invention may play an important role in the regulation of tumour development, and that molecules that can modulate the interaction of the protein of the invention with its receptor may be useful in the treatment of cancer. Also, the protein of the invention itself, in its membrane bound or its soluble form, may be useful in the treatment of cancer.

Schneider et al (Journal of Experimental Medicine volume 189 number 11 Jun. 7, 1999 pp 1747-1756) have demonstrated that B cell growth can be costimulated by the full length protein of the invention (i.e. the membrane bound form) as well as by the soluble form of the protein of the invention. Hence either form can be utilised in therapy, or to form the basis of a screen for small molecules which can modulate the interaction between the protein of the invention and its receptor.

BRIEF DESCRIPTION OF THE FIGURES

FIG. 1 shows sequence ID No. 1—the amino acid sequence of the soluble human form of the protein of the invention. Receptor binding sites are shown in bold, and potential N-linked glycosylation sites are marked with a dot.

FIG. 2 shows sequence ID No. 2—the amino acid sequence of the human membrane bound form of the protein of the invention, which comprises within it the soluble form of Seq ID No. 1. Annotations are as for FIG. 1. The transmembrane sequence is underlined.

FIG. 3 shows sequence ID No. 3—the cDNA nucleotide sequence which encodes the amino acid sequence of Seq ID No. 9, aligned to the amino acid sequence of Seq ID No. 9. Receptor binding regions are boxed, and potential N-linked glycosylation sites are marked with a dot.

FIG. 4 shows sequence ID No. 4—the cDNA nucleotide sequence which encodes the amino acid sequence of Seq ID No. 10, aligned with the amino acid sequence of Seq ID No. 10. Annotations are as for FIG. 3. The transmembrane sequence is underlined.

FIG. 5 shows sequence ID No. 5—the amino acid sequence of the soluble mouse form of the protein of the invention. The N-linked glycosylation site is marked with a dot.

FIG. 6 shows sequence ID No. 6—the amino acid sequence of the mouse membrane bound form of the protein of the invention. Annotations are as for FIG. 5. The transmembrane region is underlined.

FIG. 7 shows sequence ID No. 7—the cDNA nucleotide sequence that encodes the amino acid sequence of Seq ID No. 5, aligned with the amino acid sequence of Seq ID No. 5. Annotations are as for FIG. 5.

FIG. 8 shows sequence ID No. 8—the cDNA nucleotide sequence that encodes the amino acid sequence of Seq ID No. 6, aligned with the amino acid sequence of Seq ID No. 6. Annotations are as for FIG. 6.

FIG. 9 shows an alignment between the mouse and human forms of the full length form of the protein of the invention. (Seq ID No. 2 and Seq ID No. 6)

Figure 10A:
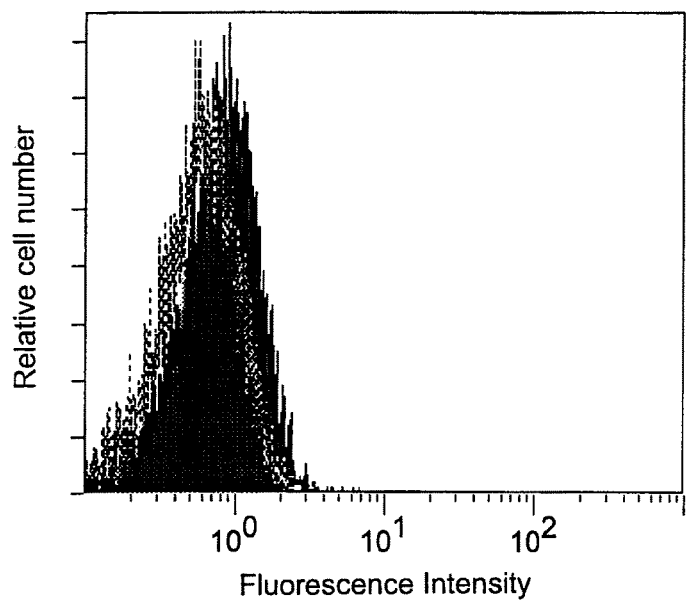
FIG. 10 Shows analysis of induction of CD40 in the presence (shaded) or absence (unshaded) of the recombinant soluble human form of the protein of the invention (A) or IL-4 (B).
Figure 10B:
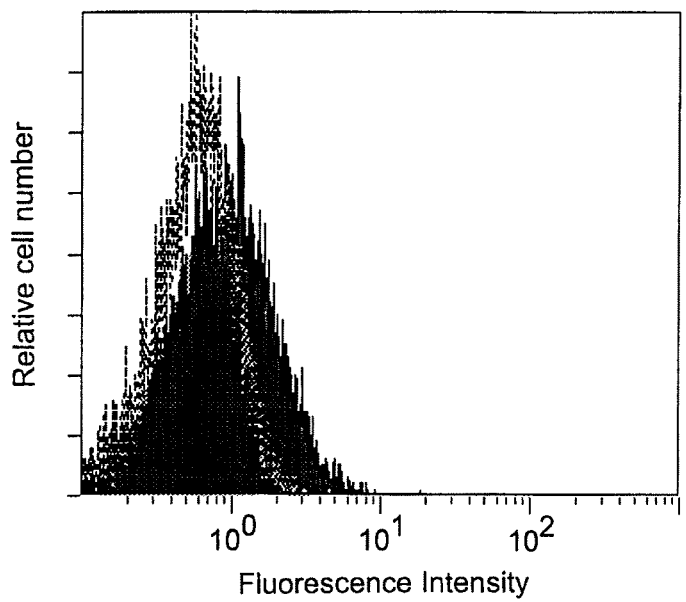

Throughout the examples:
the protein having the amino acid sequence as shown in FIG. 1 will be termed soluble D7 ligand, and the protein having the amino acid sequence as shown in FIG. 2 will be termed D7 ligand.

EXAMPLE 1

Use of Soluble D7 Ligand in a Screen to Identify Compounds that Modulate the Interaction Between the D7 Ligand and its Receptor All Incubations are Done at Room Temperature Costar RIA/EIA high binding plates are coated with goat anti-human IgG (Sigma I3382) at 2 μg/ml in PBS overnight. The coating antibody is removed, and the plates are blocked for at least 2 hours in PBS/2% (w/v) BSA. Plates are then washed three times with PBS/0.1% (v/v) Tween20.

100 μl receptor-Fc (1 μg/ml) in PBS/1% (w/v) BSA/0.1% (v/v) Tween20 is added, and plates are incubated for 1 hour. Plates are washed five times with PBS/0.1% (v/v) Tween20.

Biotin-soluble D7 ligand dilutions in PBS/1% BSA/0.1% Tween20 are added, and plates are incubated for 1 hour. Plates are washed five times with PBS/0.1% (v/v) Tween20.

Streptavidin alkaline phosphatase (1:1000) (Amersham RPN1234) is added, and plates are incubated for 1 hour. Plates are washed five times with PBS/0.1% (v/v) Tween20.

Binding is detected using Life Technologies amplifier solutions (19589-019).

EXAMPLE 2

A Cell Based Screen to Identify Compounds that Modulate the Interaction Between the Soluble D7 Ligand and its Receptor A general protocol for using a cell based screen to identify compounds that modulate the interaction between the soluble D7 ligand and its receptor is as follows:

A B cell line known to bind and respond to the D7 ligand is treated with recombinant soluble human D7 ligand exemplified (e.g. FLAG-shD7 as exemplified below) for a defined time.

Cells are harvested, and the response assayed (The response may be possibly proliferation, apoptosis, NF-κB activation or cytokine production). The assay enables determination of whether the addition of compounds inhibits the induction of a response in target cells.

A Specific Example is as Follows:
Soluble D7 Ligand Upregulates CD40

L3055 Burkitt's lymphoma cell line was grown on a feeder layer of human foetal fibroblast cells (HFF515) in L3 medium (RPMI 1640+10% Serum Supreme+antibiotics). HEK293 cells were grown in DMEM supplemented with 10% foetal calf serum and antibiotics. L3055 cells were treated either with control medium (four parts L3 medium plus one part HEK 293T cell supernatant) or with sD7 medium (four parts L3 medium plus one part cell supernatant from HEK293T cells harvested 24 hours after transient transfection with sD7) or with IL-4 (control medium plus 200 U/ml recombinant human IL-4 [Sigma]) and incubated at 37° C. for 72 hours. Cells were harvested and washed once in binding buffer then stained with FITC-conjugated mouse anti-human CD40 (Transduction Laboratories) at room temperature. The cells were then washed twice in binding buffer before analysis by flow cytometry. Induction of CD40 was observed on treatment with sD7 for 72 hours compared to the control. This assay is repeated in the presence of a molecule which inhibits or increases the induction of the response in the target cells, and the results compared. Inhibition/increase of response can be clearly demonstrated. The end result of CD40 upregulation is that B cells are signalled for growth and differentiation. Thus, this experiment supports a role for the D7 ligand in the management of immune responses, and in diseases of the immune system such as inflammation.

EXAMPLE 3

Synthesis and Purification of the Soluble D7 Ligand

Nucleic acid encoding the soluble human D7 ligand (amino acids 133 to 285) was generated by PCR using the cloned full-length open reading frame as a template.

Nucleic acid encoding the soluble human ligand D7 was cloned into vector pFLAG-CMV-1 (Kodak) (containing a CMV promoter, a preprotrypsin leader sequence, an amino-terminal FLAG epitope and a human growth hormone polyA addition sequence) to form construct pFLAG-CMV-1-hsD7.

$5 \times 10^6$ HEK 293T cells were resuspended in 250 µl cytomix (120 mM KCl; 0.15 mM $CaCl_2$; 10 mM $K_2HPO_4/KH_2PO_4$, pH 7.6; 25 mM Hepes, pH 7.6; 2 mM EGTA, pH7.6; 5 mM $MgCl_2$; 2 mM ATP; 5 mM glutathione; pH adjusted with KOH) containing 25 µg pFLAG-CMV-1-hsD7. Transfection was carried out by using a BioRad gene pulser (960 µF, 270V).

Following transfection, cells were left on ice for 10 min, then transferred to a 75 $cm^2$ tissue culture flask containing 15 ml medium (DMEM, 10% FCS, 2 mM L-glutamine, penicillin (5 µg/ml) and streptomycin (5 µg/ml)). Medium containing secreted ligand was harvested after 48 h and applied to an affinity chromatography column containing anti-FLAG M2 antibody coupled to agarose (Kodak). This was washed with Tris-buffered saline (pH 7.4) and fractions were eluted in 0.1M citrate buffer (pH 2.5). Fractions were immediately neutralised with 0.2 volumes 1M Tris.HCl (pH 7.6). Fractions containing a human soluble D7 ligand linked to the FLAG epitope (FLAG-hsD7) were identified by Western blotting using M2 anti-FLAG antibody. These fractions were pooled, and concentrated using a Centricon Plus-20 (NWML 5000) column (Millipore). FLAG-hsD7 ligand was stored at −700

EXAMPLE 4

Synthesis and Purification of the D7 Ligand

The open reading frame of human D7 ligand is cloned into vector pcDNA3 (containing a CMV promoter and a bovine growth hormone polyA addition signal) to form construct pcDNA3-hD7.

Plasmid pcDNA3-hD7 is transiently transfected by electroporation into HEK 293T cells (protocol as in example 3).

Cells are harvested after 48 h, and homogenised using a Dounce homogeniser in three volumes of protein extraction buffer (25 mM Hepes pH 7.4, 0.5% Triton-X-100, 1 "complete" protease inhibitor cocktail tablet (Boehringer Mannheim) per 50 ml buffer).

The D7 ligand is purified by affinity chromatography using anti-D7 antibody coupled to agarose.

EXAMPLE 5

Northern Blot Analysis of the Tissue Distribution of the D7 Ligand cDNA coding for human D7 ligand was excised from pcDNA3-hD7 (see example 4) with the restriction enzymes BamH1 and XbaI. This cDNA fragment was labelled with $^{32}P$ dCTP using the Amersham ready-prime system according to the manufacturers protocol. A 5 µl aliquot of this mixture was mixed with 10 ml Expresshyb solution (Clontech 8015-1) and the resulting mixture was incubated with one of the following clontech blots: Mouse (7762-1), Human-1 (#7760), Human Cancer Cell line (#7757) or Human Immune System II (#7768-1); for 2 hours at 65° C. with shaking. The probe solution was then removed and the blot was washed successively with 2×SSC (saline sodium citrate), 0.05% SDS at room temperature for three 20 minute periods. This was followed with one wash with 0.1% SSC, 0.1% SDS at room temperature. The blot was then exposed to Kodak XAR-5 film at −70° C. for 48 hours.

Figure 11A:
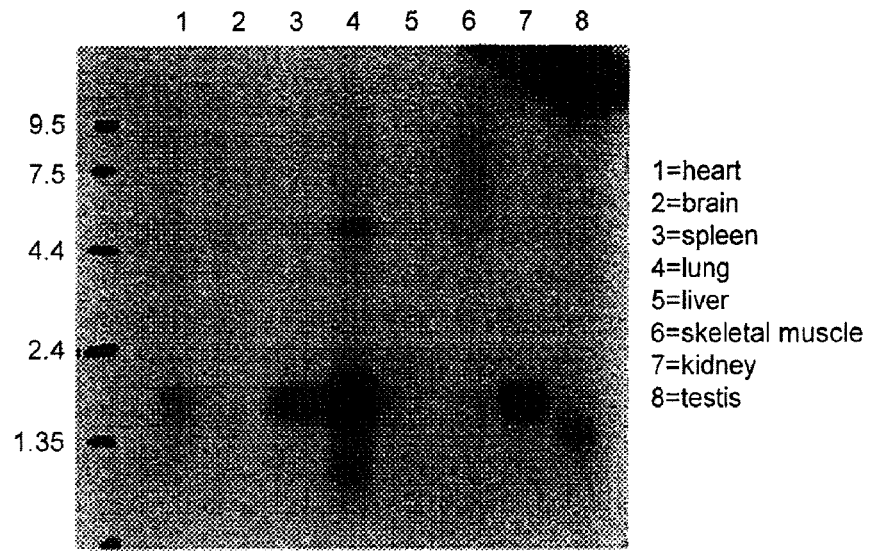
FIG. 11 shows Northern Blot analysis of the tissue specific expression of the protein of the invention in normal mouse (A) and human tumour cell lines (B). (B) tissues.
Figure 11B:
Figure 12A:
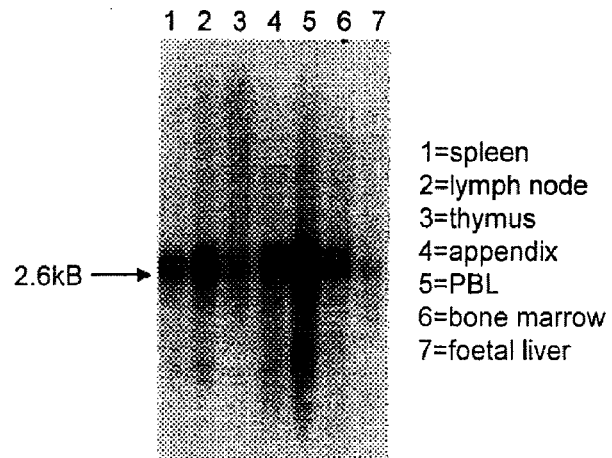
FIG. 12 shows Northern Blot analysis of the tissue specific expression of the protein of the invention in immune related tissue (A) and human tumour cell lines (B).
Figure 12B:
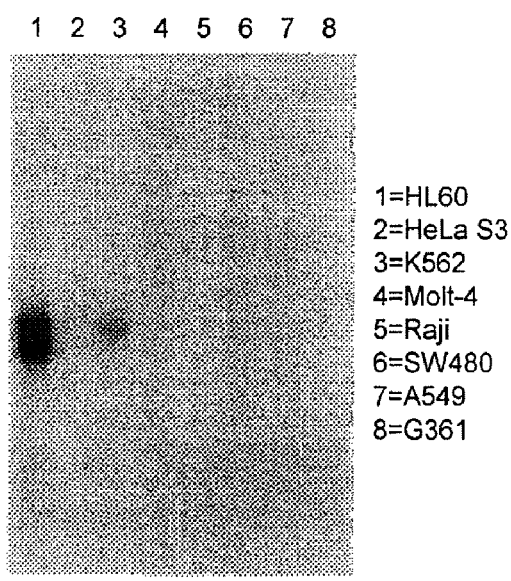

The results of the Northern blot analysis show that D7 ligand RNA is expressed in heart, lung, spleen, kidney and skeletal muscle but not brain in both mice (FIG. 11A) and humans (FIG. 11B). A blot of immune-related tissues demonstrates strong expression of D7 ligand RNA in spleen, lymph node, thymus, appendix, bone marrow and peripheral blood leukocytes (FIG. 12A) supporting its potential role as a regulator of immune system functions. Analysis of RNA from a range of human tumour cell lines shows expression of D7 ligand RNA in HL-60 promyelocytic leukaemia cells but not in a range of other tumour cell lines (FIG. 12B). The presence of D7 ligand in a leukaemic cell line also supports the fact that the D7 ligand is involved in immune system regulation and disorders.

EXAMPLE 6

Detection of Cell Surface Binding of FLAG-sD7

$10^6$ cells were incubated with 50 ng FLAG-hsD7 ligand (see example 3) in binding buffer (PBS/2.5% FCS/0.1% sodium azide) for 10 minutes at room temperature. After washing once in binding buffer, cells were incubated with 1 µg anti-FLAG M2 antibody for 10 minutes at room temperature. Cells were washed once in binding buffer, then incubated with 150 µg phycoerythrin-conjugated anti-mouse antibody for 10 minutes at room temperature. Following two further washes in binding buffer, flow cytometry was performed using a Coulter XL benchtop flow cytometer and data were collected on 10⁴ viable cells.

Figure 13:
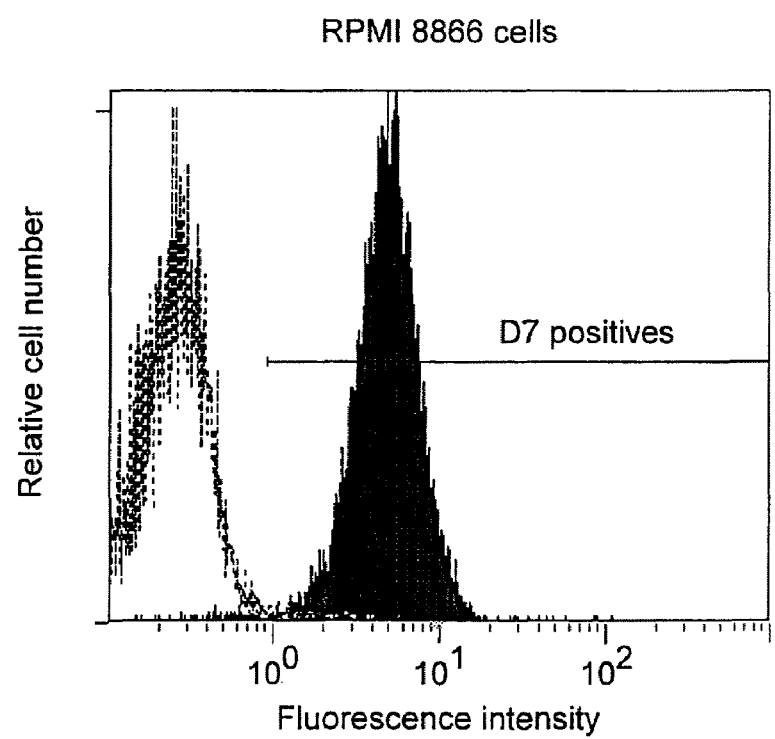
FIG. 13 shows cell binding data of FLAG-sD7 (as defined in example 3 below). The shaded area indicates binding to the B-cell lymphoma cell line RPMI 8866. In the absence of FLAG-sD7 no binding is seen (dotted line)

Results of one such experiment are shown in FIG. 13. No significant signal was detectable when any of the lines tested were treated with anti-FLAG M2 antibody and R-phyco-erythrin-conjugated second antibody only, but after prior treatment with FLAG-sD7, the signal clearly demonstrates that FLAG-hsD7 binds to the B lymphoma cell line RPMI 8866. Experiments with other cell lines have shown that FLAG-hsD7 binds two other B cell lines (RPMI 8226 and Raji) but does not bind to the T cell lines H9 and Jurkat, or the myelomonocytic lineage lines HL-60, U937 or THP-1. These results show that the extracellular domain of human D7 ligand binds to B cells, supporting its potential role in regulation of the immune system, and also suggesting that expression of the D7 receptor is restricted to B cells.

EXAMPLE 7

Detection of Cell Surface Binding of Flag-sD7 in Whole Blood

Figure 14A:
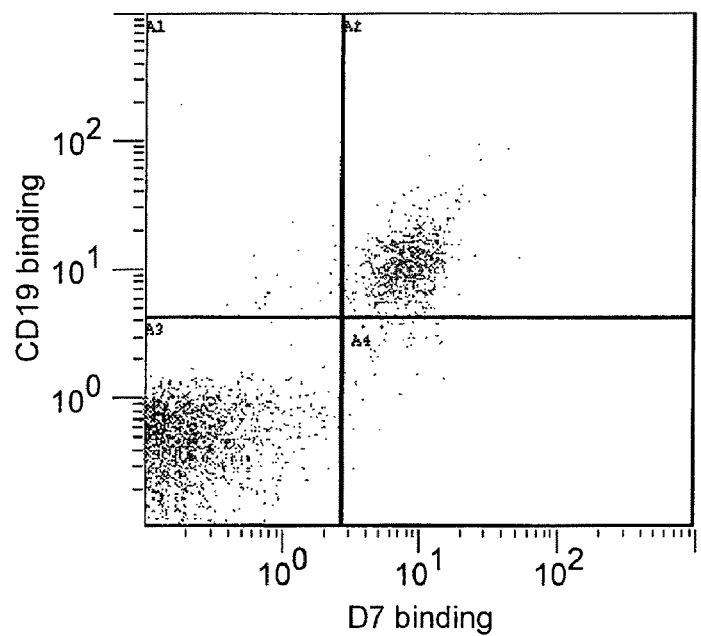
FIG. 14 shows binding of the FLAG-sD7 to CD19+ Bcells (A) and CD3+ Tcells (B) in whole blood, demonstrating the specificity of binding, to B cells only.
Figure 14B:
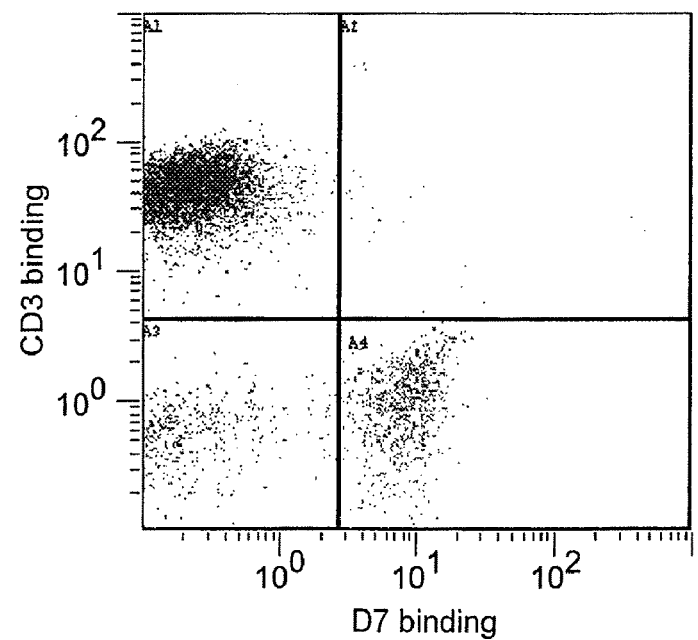

Whole blood from healthy volunteers was diluted 1:10 with 3.8% (w/v) sodium citrate. 100 ul was used in each binding assay. Cell surface binding of FLAG-sD7 was detected as in example 6, except that the second antibody was Alexa 488-conjugated anti-mouse IgG (Molecular Probes) and, after one wash, cells were incubated with 1 µg PE-conjugated mouse anti-human CD3 (Becton Dickinson) or PE-conjugated mouse anti-human CD19 (Coulter-Immunotech). This experiment confirms the specificity of binding of FLAG-sD7 demonstrated in Example 6. From FIG. 13 it can be seen that although both B cells and T cells were present, FLAG-sD7 bound only the CD19+ Bcells (FIG. 14 A), and not the CD3+ Tcells (FIG. 14 B). This confirms the specificity of binding to B cells seen with cell lines, and again suggests that expression of the D7 receptor is restricted to B cells.

EXAMPLE 8

FLAG-sD7 is Able to Trimerise

Figure 15A:
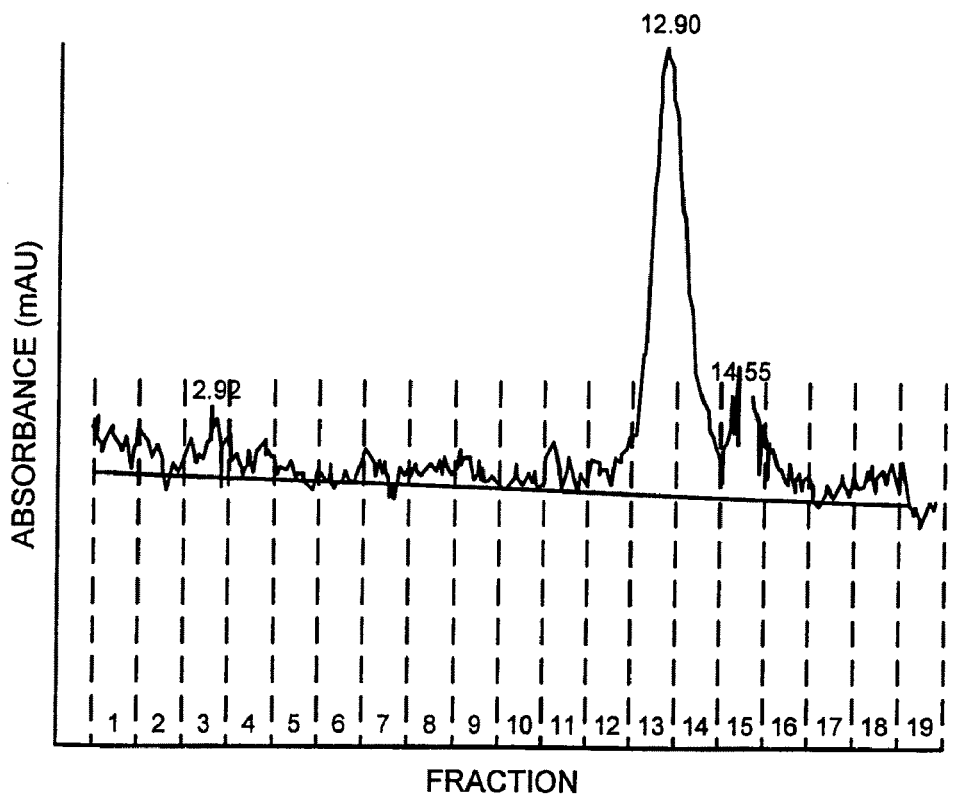
FIG. 15 shows gel filtration of recombinant FLAG-sD7, and the subsequent SDS-PAGE analysis of the fractions shown to contain protein. These results indicate that the soluble form of the protein of the invention is able to trimerise.
Figure 15B:
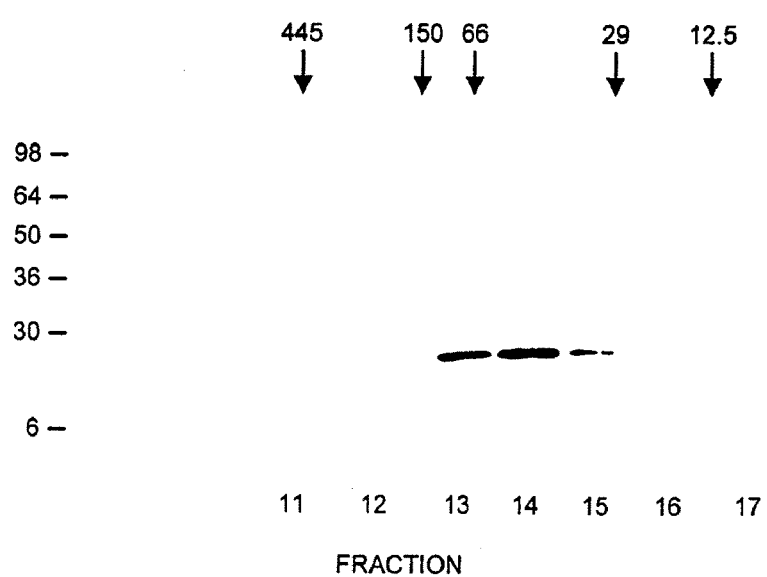

Purified recombinant FLAG-sD7 was fractionated on a Superose 12 column (Pharmacia). Proteins were eluted in PBS and fractions (1 ml) were analysed by Western blotting using anti-FLAG M2 antibody (Sigma). The column was calibrated with standard proteins: apoferritin (443 kDa), b-amylase (200 kDa), ADH (150 kDa), BSA (66 kDa), carbonic anhydrase (29 kDa) and cytochrome C (12.5 kDa). FIG. 15 A shows the eluate from the column. FIG. 15 B shows the fractions containing the peaks seen in FIG. 15A run on an SDS-PAGE. The SDS-PAGE markers are on the left hand side, indicating that the denatured protein runs at approximately 22 kDa. The markers on the top of the gel are the standard proteins used to calibrate the column, and they show that FLAG-sD7 elutes in the gel filtration fractions corresponding to a molecular weight of approximately 70 to 25 kDa. These experiments demonstrate that FLAG-sD7 is able to assemble correctly into a homotrimer, with molecular weight approximately 3×22 kDa.

EXAMPLE 9

FISH Mapping of the D7 Ligand

Lymphocytes isolated from human blood were cultured in a-minimal essential medium (a-MEM) supplemented with 10% foetal calf serum and phytohemagglutinin at 37° C. for 68-72 hours. The lymphocyte cultures were treated with BrdU (0.18 mg/ml Sigma) to synchronise the cell population. The synchronised cells were washed three times with serum free medium to release the block and recultured at 37° C. for 6 hours in a-MEM with thymidine (2.5 µg/ml Sigma). Cells were harvested and slides were made by using standard procedures including hypotonic treatment, fixation and air-dry.

Slides were baked at 55° C. for 1 hour. After RNase treatment, the slides were denatured in 70% formamide in 2×SSC for 2 min at 70° C. followed by dehydration with ethanol. D7-27 DNA probe which is the full length D7 cDNA as shown in FIG. 4, plus 150 nucleotides of 5' untranslated region and 50 nt of 3' untranslated region) was biotinylated with dATP, and probes were denatured at 75° C. for 5 min. in a hybridisation mix consisting of 50% formamide and 10% dextran sulphate. Probes were loaded on the denatured chromosomal slides. After over night hybridisation, slides were washed and detected as well as amplified. FISH signals and the DAPI banding was recorded separately by taking photographs, and the assignment of the FISH mapping data with chromosomal bands was achieved by superimposing DISH signals with DAPI banded chromosomes. The DAPI banding showed that the signal mapped to human chromosome 13, and the FISH results further mapped it to region q33.

We claim:

1. A method of inhibiting the interaction in a mammal between a receptor on B-cells and a homotrimeric polypeptide comprising a polypeptide having 99% sequence identity to SEQ ID NO: 1, said method comprising administering to said mammal an antibody that specifically binds a polypeptide consisting of SEQ ID NO: 1 in trimeric form.

2. The method as claimed in claim 1, wherein said mammal is a human.

3. The method as claimed in claim 1, wherein said antibody is a monoclonal antibody.

4. A method of inhibiting the binding of a receptor on B-cells with a homotrimeric polypeptide comprising a polypeptide having 99% sequence identity to SEQ ID NO: 1, said method comprising contacting said homotrimeric polypeptide with an antibody that specifically binds a polypeptide consisting of SEQ ID NO: 1 in trimeric form.

5. The method as claimed in claim 4, wherein said antibody is a monoclonal antibody.

* * * * *

```
SEQUENCE LISTING

<160> NUMBER OF SEQ ID NOS: 10

<210> SEQ ID NO 1
<211> LENGTH: 153
<212> TYPE: PRT
<213> ORGANISM: Homo sapiens

<400> SEQUENCE: 1

Arg Ala Val Gln Gly Pro Glu Glu Thr Val Thr Gln Asp Cys Leu Gln
1               5                   10                  15

Leu Ile Ala Asp Ser Glu Thr Pro Thr Ile Gln Lys Gly Ser Tyr Thr
            20                  25                  30

Phe Val Pro Trp Leu Leu Ser Phe Lys Arg Gly Ser Ala Leu Glu Glu
        35                  40                  45

Lys Glu Asn Lys Ile Leu Val Lys Glu Thr Gly Tyr Phe Phe Ile Tyr
```

```
            50                  55                  60
Gly Gln Val Leu Tyr Thr Asp Lys Thr Tyr Ala Met Gly His Leu Ile
 65                  70                  75                  80

Gln Arg Lys Lys Val His Val Phe Gly Asp Glu Leu Ser Leu Val Thr
                 85                  90                  95

Leu Phe Arg Cys Ile Gln Asn Met Pro Glu Thr Leu Pro Asn Asn Ser
            100                 105                 110

Cys Tyr Ser Ala Gly Ile Ala Lys Leu Glu Glu Gly Asp Glu Leu Gln
            115                 120                 125

Leu Ala Ile Pro Arg Glu Asn Ala Gln Ile Ser Leu Asp Gly Asp Val
            130                 135                 140

Thr Phe Phe Gly Ala Leu Lys Leu Leu
145                 150
```

<210> SEQ ID NO 2
<211> LENGTH: 285
<212> TYPE: PRT
<213> ORGANISM: Homo sapiens

<400> SEQUENCE: 2

```
Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
                 20                  25                  30

Arg Lys Glu Ser Pro Ser Val Arg Ser Ser Lys Asp Gly Lys Leu Leu
             35                  40                  45

Ala Ala Thr Leu Leu Leu Ala Leu Leu Ser Cys Cys Leu Thr Val Val
         50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Val Thr Gln
            130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
            210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
```

<210> SEQ ID NO 3
<211> LENGTH: 462
<212> TYPE: DNA
<213> ORGANISM: Homo sapiens
<220> FEATURE:
<221> NAME/KEY: CDS
<222> LOCATION: (1)..(462)

<400> SEQUENCE: 3

```
cgt gcc gtt cag ggt cca gaa gaa aca gtc act caa gac tgc ttg caa    48
Arg Ala Val Gln Gly Pro Glu Glu Thr Val Thr Gln Asp Cys Leu Gln
 1               5                  10                  15 ctg att gca gac agt gaa aca cca act ata caa aaa gga tct tac aca    96
Leu Ile Ala Asp Ser Glu Thr Pro Thr Ile Gln Lys Gly Ser Tyr Thr
             20                  25                  30 ttt gtt cca tgg ctt ctc agc ttt aaa agg gga agt gcc cta gaa gaa   144
Phe Val Pro Trp Leu Leu Ser Phe Lys Arg Gly Ser Ala Leu Glu Glu
         35                  40                  45 aaa gag aat aaa ata ttg gtc aaa gaa act ggt tac ttt ttt ata tat   192
Lys Glu Asn Lys Ile Leu Val Lys Glu Thr Gly Tyr Phe Phe Ile Tyr
     50                  55                  60 ggt cag gtt tta tat act gat aag acc tac gcc atg gga cat cta att   240
Gly Gln Val Leu Tyr Thr Asp Lys Thr Tyr Ala Met Gly His Leu Ile
 65                  70                  75                  80 cag agg aag aag gtc cat gtc ttt ggg gat gaa ttg agt ctg gtg act   288
Gln Arg Lys Lys Val His Val Phe Gly Asp Glu Leu Ser Leu Val Thr
                 85                  90                  95 ttg ttt cga tgt att caa aat atg cct gaa aca cta ccc aat aat tcc   336
Leu Phe Arg Cys Ile Gln Asn Met Pro Glu Thr Leu Pro Asn Asn Ser
            100                 105                 110 tgc tat tca gct ggc att gca aaa ctg gaa gaa gga gat gga ctc caa   384
Cys Tyr Ser Ala Gly Ile Ala Lys Leu Glu Glu Gly Asp Gly Leu Gln
        115                 120                 125 ctt gca ata cca aga gaa aat gca caa ata tca ctg gat gga gat gtc   432
Leu Ala Ile Pro Arg Glu Asn Ala Gln Ile Ser Leu Asp Gly Asp Val
    130                 135                 140 aca ttt ttt ggt gca ttg aaa ctg ctg tga                           462
Thr Phe Phe Gly Ala Leu Lys Leu Leu
145                 150
```

<210> SEQ ID NO 4
<211> LENGTH: 858
<212> TYPE: DNA
<213> ORGANISM: Homo sapiens
<220> FEATURE:
<221> NAME/KEY: CDS
<222> LOCATION: (1)..(858)

<400> SEQUENCE: 4

```
atg gat gac tcc aca gaa agg gag cag tca cgc ctt act tct tgc ctt    48
Met Asp Asp Ser Thr Glu Arg Glu Gln Ser Arg Leu Thr Ser Cys Leu
 1               5                  10                  15 aag aaa aga gaa gaa atg aaa ctg aag gag tgt gtt tcc atc ctc cca    96
Lys Lys Arg Glu Glu Met Lys Leu Lys Glu Cys Val Ser Ile Leu Pro
             20                  25                  30 cgg aag gaa agc ccc tct gtc cga tcc tcc aaa gac gga aag ctg ctg   144
Arg Lys Glu Ser Pro Ser Val Arg Ser Ser Lys Asp Gly Lys Leu Leu
         35                  40                  45 gct gca acc ttg ctg ctg gca ctg ctg tct tgc tgc ctc acg gtg gtg   192
Ala Ala Thr Leu Leu Leu Ala Leu Leu Ser Cys Cys Leu Thr Val Val
     50                  55                  60
```

```
tct ttc tac cag gtg gcc gcc ctg caa ggg gac ctg gcc agc ctc cgg      240
Ser Phe Tyr Gln Val Ala Ala Leu Gln Gly Asp Leu Ala Ser Leu Arg
 65              70                  75                  80 gca gag ctg cag ggc cac cac gcg gag aag ctg cca gca gga gca gga      288
Ala Glu Leu Gln Gly His His Ala Glu Lys Leu Pro Ala Gly Ala Gly
                 85                  90                  95 gcc ccc aag gcc ggc ctg gag gaa gct cca gct gtc acc gcg gga ctg      336
Ala Pro Lys Ala Gly Leu Glu Glu Ala Pro Ala Val Thr Ala Gly Leu
            100                 105                 110 aaa atc ttt gaa cca cca gct cca gga gaa ggc aac tcc agt cag aac      384
Lys Ile Phe Glu Pro Pro Ala Pro Gly Glu Gly Asn Ser Ser Gln Asn
        115                 120                 125 agc aga aat aag cgt gcc gtt cag ggt cca gaa gaa aca gtc act caa      432
Ser Arg Asn Lys Arg Ala Val Gln Gly Pro Glu Glu Thr Val Thr Gln
130                 135                 140 gac tgc ttg caa ctg att gca gac agt gaa aca cca act ata caa aaa      480
Asp Cys Leu Gln Leu Ile Ala Asp Ser Glu Thr Pro Thr Ile Gln Lys
145                 150                 155                 160 gga tct tac aca ttt gtt cca tgg ctt ctc agc ttt aaa agg gga agt      528
Gly Ser Tyr Thr Phe Val Pro Trp Leu Leu Ser Phe Lys Arg Gly Ser
                165                 170                 175 gcc cta gaa gaa aaa gag aat aaa ata ttg gtc aaa gaa act ggt tac      576
Ala Leu Glu Glu Lys Glu Asn Lys Ile Leu Val Lys Glu Thr Gly Tyr
            180                 185                 190 ttt ttt ata tat ggt cag gtt tta tat act gat aag acc tac gcc atg      624
Phe Phe Ile Tyr Gly Gln Val Leu Tyr Thr Asp Lys Thr Tyr Ala Met
        195                 200                 205 gga cat cta att cag agg aag aag gtc cat gtc ttt ggg gat gaa ttg      672
Gly His Leu Ile Gln Arg Lys Lys Val His Val Phe Gly Asp Glu Leu
210                 215                 220 agt ctg gtg act ttg ttt cga tgt att caa aat atg cct gaa aca cta      720
Ser Leu Val Thr Leu Phe Arg Cys Ile Gln Asn Met Pro Glu Thr Leu
225                 230                 235                 240 ccc aat aat tcc tgc tat tca gct ggc att gca aaa ctg gaa gaa gga      768
Pro Asn Asn Ser Cys Tyr Ser Ala Gly Ile Ala Lys Leu Glu Glu Gly
                245                 250                 255 gat gga ctc caa ctt gca ata cca aga gaa aat gca caa ata tca ctg      816
Asp Gly Leu Gln Leu Ala Ile Pro Arg Glu Asn Ala Gln Ile Ser Leu
            260                 265                 270 gat gga gat gtc aca ttt ttt ggt gca ttg aaa ctg ctg tga              858
Asp Gly Asp Val Thr Phe Phe Gly Ala Leu Lys Leu Leu
        275                 280                 285

<210> SEQ ID NO 5
<211> LENGTH: 144
<212> TYPE: PRT
<213> ORGANISM: Mus sp.

<400> SEQUENCE: 5

Ile Ile Gln Asp Cys Leu Gln Leu Ile Ala Asp Ser Asp Thr Pro Thr
 1               5                  10                  15

Ile Arg Lys Gly Thr Tyr Thr Phe Val Pro Trp Leu Leu Ser Phe Lys
                20                  25                  30

Arg Gly Asn Ala Leu Glu Glu Lys Glu Asn Lys Ile Val Val Arg Gln
            35                  40                  45

Thr Gly Tyr Phe Phe Ile Tyr Ser Gln Val Leu Tyr Thr Asp Pro Ile
        50                  55                  60

Phe Ala Met Gly His Val Ile Gln Arg Lys Lys Val His Val Phe Gly
 65                  70                  75                  80

Asp Glu Leu Ser Leu Val Thr Leu Phe Arg Cys Ile Gln Asn Met Pro
```

```
                   85                  90                  95
Lys Thr Leu Pro Asn Asn Ser Cys Tyr Ser Ala Gly Ile Ala Arg Leu
            100                 105                 110

Glu Glu Gly Asp Glu Ile Gln Leu Ala Ile Pro Arg Glu Asn Ala Gln
            115                 120                 125

Ile Ser Arg Asn Gly Asp Asp Thr Phe Phe Gly Ala Leu Lys Leu Leu
        130                 135                 140

<210> SEQ ID NO 6
<211> LENGTH: 309
<212> TYPE: PRT
<213> ORGANISM: Mus sp.

<400> SEQUENCE: 6

Met Asp Glu Ser Ala Lys Thr Leu Pro Pro Cys Leu Cys Phe Cys
  1               5                  10                  15

Ser Glu Lys Gly Glu Asp Met Lys Val Gly Tyr Asp Pro Ile Thr Pro
             20                  25                  30

Gln Lys Glu Glu Gly Ala Trp Phe Gly Ile Cys Arg Asp Gly Arg Leu
         35                  40                  45

Leu Ala Ala Thr Leu Leu Ala Leu Leu Ser Ser Phe Thr Ala
     50                  55                  60

Met Ser Leu Tyr Gln Leu Ala Ala Leu Gln Ala Asp Leu Met Asn Leu
 65                  70                  75                  80

Arg Met Glu Leu Gln Ser Tyr Arg Gly Ser Ala Thr Pro Ala Ala Ala
                 85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
            115                 120                 125

Gln Gly Pro Glu Glu Thr Glu Gln Asp Val Asp Leu Ser Ala Pro Pro
        130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
                260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
        290                 295                 300

Ala Leu Lys Leu Leu
305
```

```
<210> SEQ ID NO 7
<211> LENGTH: 435
<212> TYPE: DNA
<213> ORGANISM: Mus sp.
<220> FEATURE:
<221> NAME/KEY: CDS
<222> LOCATION: (1)..(435)

<400> SEQUENCE: 7 atc att caa gac tgt ctg cag ctg att gca gac agc gac acg ccg act        48
Ile Ile Gln Asp Cys Leu Gln Leu Ile Ala Asp Ser Asp Thr Pro Thr
 1               5                  10                  15 ata cga aaa gga act tac aca ttt gtt cca tgg ctt ctc agc ttt aaa        96
Ile Arg Lys Gly Thr Tyr Thr Phe Val Pro Trp Leu Leu Ser Phe Lys
             20                  25                  30 aga gga aat gcc ttg gag gag aaa gag aac aaa ata gtg gtg agg caa       144
Arg Gly Asn Ala Leu Glu Glu Lys Glu Asn Lys Ile Val Val Arg Gln
         35                  40                  45 aca ggc tat ttc ttc atc tac agc cag gtt cta tac acg gac ccc atc       192
Thr Gly Tyr Phe Phe Ile Tyr Ser Gln Val Leu Tyr Thr Asp Pro Ile
     50                  55                  60 ttt gct atg ggt cat gtc atc cag agg aag aaa gta cac gtc ttt ggg       240
Phe Ala Met Gly His Val Ile Gln Arg Lys Lys Val His Val Phe Gly
 65                  70                  75                  80 gac gag ctg agc ctg gtg acc ctg ttc cga tgt att cag aat atg ccc       288
Asp Glu Leu Ser Leu Val Thr Leu Phe Arg Cys Ile Gln Asn Met Pro
                 85                  90                  95 aaa aca ctg ccc aac aat tcc tgc tac tcg gct ggc atc gcg agg ctg       336
Lys Thr Leu Pro Asn Asn Ser Cys Tyr Ser Ala Gly Ile Ala Arg Leu
            100                 105                 110 gaa gaa gga gat gag att cag ctt gca att cct cgg gag aat gca cag       384
Glu Glu Gly Asp Glu Ile Gln Leu Ala Ile Pro Arg Glu Asn Ala Gln
        115                 120                 125 att tca cgc aac gga gac gac acc ttc ttt ggt gcc cta aaa ctg ctg       432
Ile Ser Arg Asn Gly Asp Asp Thr Phe Phe Gly Ala Leu Lys Leu Leu
    130                 135                 140 taa                                                                   435

<210> SEQ ID NO 8
<211> LENGTH: 930
<212> TYPE: DNA
<213> ORGANISM: Mus sp.
<220> FEATURE:
<221> NAME/KEY: CDS
<222> LOCATION: (1)..(930)

<400> SEQUENCE: 8 atg gat gag tct gca aag acc ctg cca cca ccg tgc ctc tgt ttt tgc        48
Met Asp Glu Ser Ala Lys Thr Leu Pro Pro Pro Cys Leu Cys Phe Cys
 1               5                  10                  15 tcc gag aaa gga gaa gat atg aaa gtg gga tat gat ccc atc act ccg        96
Ser Glu Lys Gly Glu Asp Met Lys Val Gly Tyr Asp Pro Ile Thr Pro
             20                  25                  30 cag aag gag gag ggt gcc tgg ttt ggg atc tgc agg gat gga agg ctg       144
Gln Lys Glu Glu Gly Ala Trp Phe Gly Ile Cys Arg Asp Gly Arg Leu
         35                  40                  45 ctg gct gct acc ctc ctg ctg gcc ctg ttg tcc agc agt ttc aca gcg       192
Leu Ala Ala Thr Leu Leu Leu Ala Leu Leu Ser Ser Ser Phe Thr Ala
     50                  55                  60 atg tcc ttg tac cag ttg gct gcc ttg caa gca gac ctg atg aac ctg       240
Met Ser Leu Tyr Gln Leu Ala Ala Leu Gln Ala Asp Leu Met Asn Leu
 65                  70                  75                  80 cgc atg gag ctg cag agc tac cga ggt tca gca aca cca gcc gcc gcg       288
```

```
                Arg Met Glu Leu Gln Ser Tyr Arg Gly Ser Ala Thr Pro Ala Ala Ala
                                85                  90                  95 ggt gct cca gag ttg acc gct gga gtc aaa ctc ctg acg ccg gca gct            336
Gly Ala Pro Glu Leu Thr Ala Gly Val Lys Leu Leu Thr Pro Ala Ala
            100                 105                 110 cct cga ccc cac aac tcc agc cgc ggc cac agg aac aga cgc gct ttc            384
Pro Arg Pro His Asn Ser Ser Arg Gly His Arg Asn Arg Arg Ala Phe
            115                 120                 125 cag gga cca gag gaa aca gaa caa gat gta gac ctc tca gct cct cct            432
Gln Gly Pro Glu Glu Thr Glu Gln Asp Val Asp Leu Ser Ala Pro Pro
        130                 135                 140 gca cca tgc ctg cct gga tgc cgc cat tct caa cat gat gat aat gga            480
Ala Pro Cys Leu Pro Gly Cys Arg His Ser Gln His Asp Asp Asn Gly
145                 150                 155                 160 atg aac ctc aga aac atc att caa gac tgt ctg cag ctg att gca gac            528
Met Asn Leu Arg Asn Ile Ile Gln Asp Cys Leu Gln Leu Ile Ala Asp
                165                 170                 175 agc gac acg ccg act ata cga aaa gga act tac aca ttt gtt cca tgg            576
Ser Asp Thr Pro Thr Ile Arg Lys Gly Thr Tyr Thr Phe Val Pro Trp
            180                 185                 190 ctt ctc agc ttt aaa aga gga aat gcc ttg gag gag aaa gag aac aaa            624
Leu Leu Ser Phe Lys Arg Gly Asn Ala Leu Glu Glu Lys Glu Asn Lys
            195                 200                 205 ata gtg gtg agg caa aca ggc tat ttc ttc atc tac agc cag gtt cta            672
Ile Val Val Arg Gln Thr Gly Tyr Phe Phe Ile Tyr Ser Gln Val Leu
        210                 215                 220 tac acg gac ccc atc ttt gct atg ggt cat gtc atc cag agg aag aaa            720
Tyr Thr Asp Pro Ile Phe Ala Met Gly His Val Ile Gln Arg Lys Lys
225                 230                 235                 240 gta cac gtc ttt ggg gac gag ctg agc ctg gtg acc ctg ttc cga tgt            768
Val His Val Phe Gly Asp Glu Leu Ser Leu Val Thr Leu Phe Arg Cys
                245                 250                 255 att cag aat atg ccc aaa aca ctg ccc aac aat tcc tgc tac tcg gct            816
Ile Gln Asn Met Pro Lys Thr Leu Pro Asn Asn Ser Cys Tyr Ser Ala
                260                 265                 270 ggc atc gcg agg ctg gaa gaa gga gat gag att cag ctt gca att cct            864
Gly Ile Ala Arg Leu Glu Glu Gly Asp Glu Ile Gln Leu Ala Ile Pro
            275                 280                 285 cgg gag aat gca cag att tca cgc aac gga gac gac acc ttc ttt ggt            912
Arg Glu Asn Ala Gln Ile Ser Arg Asn Gly Asp Asp Thr Phe Phe Gly
        290                 295                 300 gcc cta aaa ctg ctg taa                                                    930
Ala Leu Lys Leu Leu
305

<210> SEQ ID NO 9
<211> LENGTH: 153
<212> TYPE: PRT
<213> ORGANISM: Homo sapiens

<400> SEQUENCE: 9

Arg Ala Val Gln Gly Pro Glu Glu Thr Val Thr Gln Asp Cys Leu Gln
 1               5                  10                  15

Leu Ile Ala Asp Ser Glu Thr Pro Thr Ile Gln Lys Gly Ser Tyr Thr
                20                  25                  30

Phe Val Pro Trp Leu Leu Ser Phe Lys Arg Gly Ser Ala Leu Glu Glu
            35                  40                  45

Lys Glu Asn Lys Ile Leu Val Lys Glu Thr Gly Tyr Phe Phe Ile Tyr
        50                  55                  60

Gly Gln Val Leu Tyr Thr Asp Lys Thr Tyr Ala Met Gly His Leu Ile
```

```
                65                  70                  75                  80
Gln Arg Lys Lys Val His Val Phe Gly Asp Glu Leu Ser Leu Val Thr
                    85                  90                  95

Leu Phe Arg Cys Ile Gln Asn Met Pro Glu Thr Leu Pro Asn Asn Ser
                100                 105                 110

Cys Tyr Ser Ala Gly Ile Ala Lys Leu Glu Glu Gly Asp Gly Leu Gln
            115                 120                 125

Leu Ala Ile Pro Arg Glu Asn Ala Gln Ile Ser Leu Asp Gly Asp Val
        130                 135                 140

Thr Phe Phe Gly Ala Leu Lys Leu Leu
145                 150

<210> SEQ ID NO 10
<211> LENGTH: 285
<212> TYPE: PRT
<213> ORGANISM: Homo sapiens

<400> SEQUENCE: 10

Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
                 20                  25                  30

Arg Lys Glu Ser Pro Ser Val Arg Ser Ser Lys Asp Gly Lys Leu Leu
             35                  40                  45

Ala Ala Thr Leu Leu Leu Ala Leu Leu Ser Cys Cys Leu Thr Val Val
         50                  55                  60

Ser Phe Tyr Gln Val Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Gly Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```